United States Patent [19]
Hosonuma et al.

[11] Patent Number: 5,390,530
[45] Date of Patent: Feb. 21, 1995

[54] LEAK DETECTION METHOD FOR GAS, STEAM OR THE LIKE BASED, IN PART, ON THE MEASUREMENT OF WIND DIRECTION AND VELOCITY

[75] Inventors: Akira Hosonuma, Abiko; Teruyuki Onodera, Osaka; Saburoh Takahashi, Takaishi; Kunio Sakashita, Yokohama; Yoshinori Hiroshige, Takaishi, all of Japan

[73] Assignee: Mitsui Toatsu Chemicals, Inc., Tokyo, Japan

[21] Appl. No.: 131,611

[22] Filed: Oct. 5, 1993

Related U.S. Application Data

[62] Division of Ser. No. 845,185, Mar. 3, 1992, Pat. No. 5,297,421.

[30] Foreign Application Priority Data

Mar. 5, 1991 [JP] Japan .................. 3-062482
Dec. 24, 1991 [JP] Japan .................. 3-341416

[51] Int. Cl.$^6$ ............................... G01M 3/00
[52] U.S. Cl. ............................... 73/40
[58] Field of Search ............................... 73/40, 40.7

[56] References Cited

U.S. PATENT DOCUMENTS 4,181,699 1/1980 Kitzinger .................. 422/87

FOREIGN PATENT DOCUMENTS 2943949 5/1981 Germany .
157689 12/1979 Japan .
13719 3/1980 Japan .
102134 6/1984 Japan .
100244 7/1984 Japan .
206837 12/1986 Japan .
140039 6/1989 Japan .
219533 9/1989 Japan .
21841 1/1991 Japan .

*Primary Examiner*—Hezron E. Williams
*Assistant Examiner*—Michael J. Brock
*Attorney, Agent, or Firm*—Burns, Doane, Swecker & Mathis

[57] ABSTRACT

A leak detection system for gas, steam or the like in a plant yard includes a plurality of sampling modules and wind direction and velocity indicators both arranged around apparatus or equipment in the plant yard. Samples of the atmosphere around the apparatus or equipment are drawn through the sampling modules, and the concentration of a substance leaked into the atmosphere is detected by a sensor module. At the same time, the direction and velocity of wind in the plant yard are determined. Leakage of gas, steam or the like in the plant yard can be detected based on the concentrations and wind direction and velocity. Methods for the determination of the direction and/or velocity of wind, wind direction and velocity indicators, and anemoscopes are also described.

1 Claim, 10 Drawing Sheets

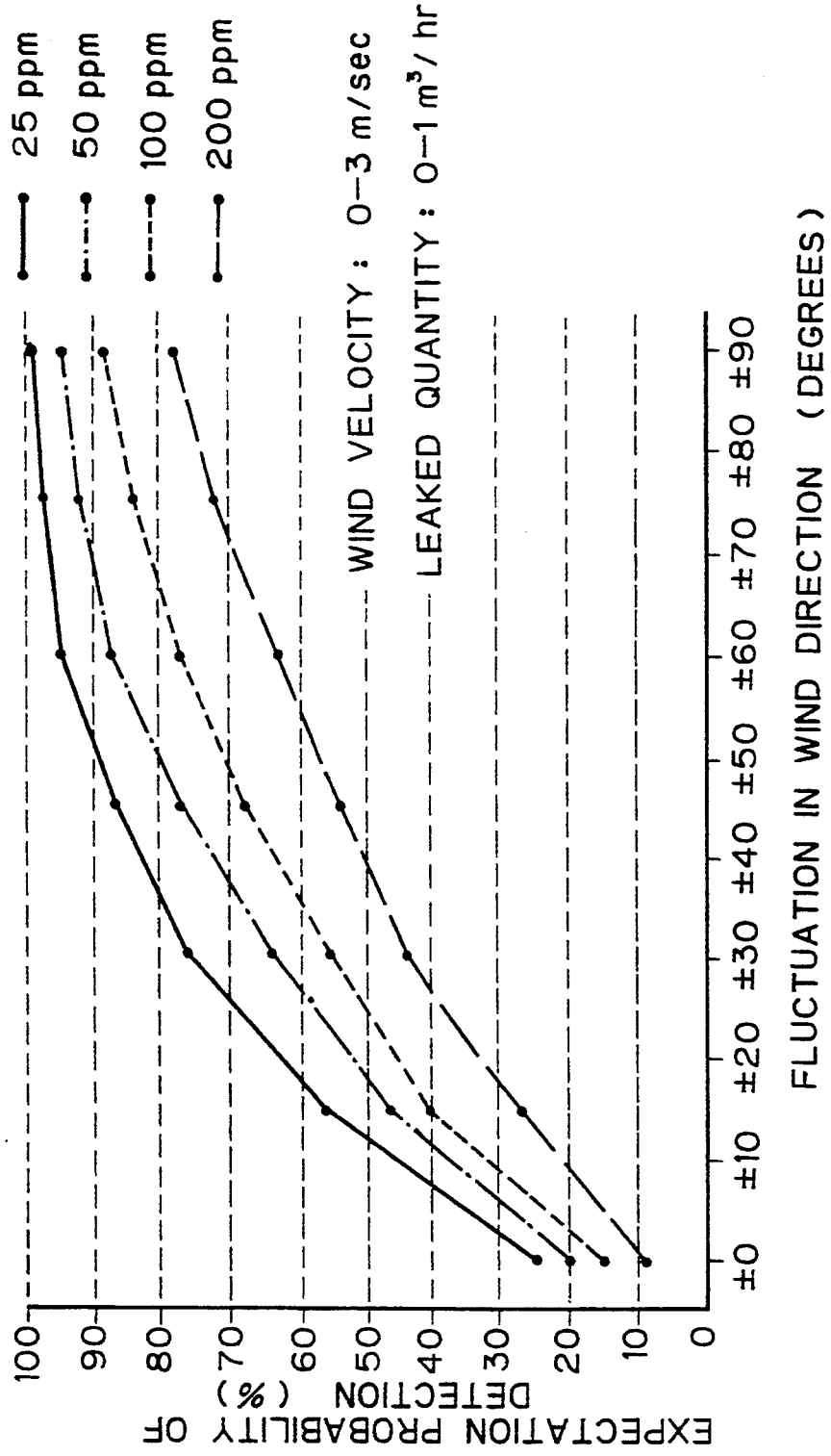

LEAK DETECTION METHOD FOR GAS, STEAM OR THE LIKE BASED, IN PART, ON THE MEASUREMENT OF WIND DIRECTION AND VELOCITY

This application is a divisional of application Ser. No. 07/845,185, filed Mar. 3, 1992, now patent No. 5,297,421. 5,297,421.

BACKGROUND OF THE INVENTION

1. Field of the Invention

This invention relates to a leak detection system for gas, steam or the like, said system being suitable for the detection of gas, steam or the like leaking from equipment or apparatus of a plant where a flammable or noxious substance is handled in a gaseous, liquid or solid form, as well as to a method for the measurement of the direction and velocity of local wind, said measurement being needed for the estimation of a leak point and leak quantity, and an instrument for the determination of wind direction and velocity.

2. Description of the Related Art

From every country there are reports of serious accidents or disasters caused by fire, explosion or leakage of noxious gas from individual machines, equipment or facilities, arising at factories with a plurality of machinery, equipment and/or facilities connected together via pipes, or in industrial complexes where a conglomeration of such factories is systematically linked one to another. Damage caused by such incidents is not limited to the loss of facilities and/or interruption of production. For example, accidents at nuclear power plants and the like where radioactive substances are handled involve such potential danger that they may even lead to global contamination.

Causes of accidents include those pertaining to human error in operation and those attributed to a failure of machinery, equipment or facilities. In a large majority of reported incidents, leakage of gas or the like actually took place as an initial phenomenon; the gas so leaked then igniting due to the existence of a certain ignition source, resulting in fire or explosion.

It is, therefore, possible to obviate many of such accidents and to minimize the loss of property of the society, if leakage of gas or the like can be discovered and stopped in an early stage, when the quantity of leakage is still small.

With the foregoing objective in view, business establishments beyond a certain size are required to install gas leak detectors under laws such as the Fire Protection Law and High Pressure Gas Control Law in Japan. In particular, according to Section 8, No. 53 of the Safety Regulations for Industrial Complexes in the latter law, it is specifically ruled that gas leak detectors of a prescribed specification be installed at intervals of 20 m, with at least one gas leak detector at each point of installation along the boundary of each plant or the like.

Besides these statutory regulations, business establishments which manage factories or various facilities have of their own volition also exercised tremendous efforts for the early discovery of leakage of gas.

To date there exists neither a highly reliable leak detection method for the discovery of leakage of gas, steam or the like nor a system for estimating the point, quantity and the like of leakage when such leakage is discovered. Indeed, such detection is commonly dependent only on discovery by a maintenance crew member on regular patrol in a plant in an effort to discover any abnormality.

Under these circumstances, the probability of detection of gas leakage in a plant by plural gas detectors discretely arranged in the plant is therefore very low. Moreover, even if a detector provides a warning, the retention of a warning signal may be brief and often becomes intermittent. It is, therefore, difficult to determine if the warning results from the discovery of a real leakage or is caused by some noise or is due to drifting of the zero point and, under the circumstances, the detection of gas leakage relies upon human judgment.

It is typical for conventional wind direction and velocity indicators to be in the form of a model plane which rotates horizontally around a vertical axis, and to be equipped with a propeller at a free end of a horizontal portion. In general, owing to the provision of a tail, the direction of the main body of the plane is brought into conformity with the direction of wind so that this directional change indicates the wind direction. Further, the propeller rotates at a revolution speed proportional to the velocity of the wind and the resulting rotation is transmitted to a small generator accommodated inside the main body of the plane. The wind velocity is therefore indicated by the output voltage of the generator.

The conventional wind direction and velocity indicators of the type described above are however accompanied by the drawback that they do not operate sufficiently well at low wind velocities. At a wind velocity not higher than 1 m/sec, for example, rotation is so slow that the accuracy of indication of the wind direction and velocity becomes poor. Further, at 0.5 m/sec or lower, the propeller virtually stops, thereby making the measurement no longer feasible.

Another drawback of the conventional type resides in the difficulty in constructing the indicators in an explosion-proof form which enables them to be used in an atmosphere having potential fire and/or explosion hazard, and this difficulty limits their use at places where a chemical reagent, petroleum product, gaseous fuel or the like is handled. Although their production in an explosion-proof structure is feasible, this leads to the disadvantages that they are expensive and, if a seal is provided between a propeller and a small generator as a common means for providing an explosion-proof construction, the resultant extra friction further downgrades the accuracy of wind velocity measurements.

Although the need for the measurement of wind velocities as low as 1 m/sec and slower in the field of general meteorological observation is not referred to in the present specification, there is an increasing demand for the high-accuracy measurement of such low wind velocities in order to determine the wind direction and velocity for environmental assessment at factories, offices and the like, especially in order to predict the state of diffusion of noxious gas, steam or the like at such places in the event of its leakage and also to estimate the point of the leakage. Further, to measure the wind direction and velocity in such a case, it is essential to employ wind direction and velocity indicators which are usable in an atmosphere having potential fire and/or explosion hazard or can be modified into an explosion-proof construction without impairing their measurement accuracy.

SUMMARY OF THE INVENTION

An object of this invention is, therefore, to provide a highly reliable leak detection system for gas, steam and the like.

Another object of this invention is to provide a method for the precise determination of the direction and velocity of wind even if the velocity of the wind is low.

A further object of this invention is to provide a wind direction and velocity indicator which is in an inherently of explosion-proof construction or can be easily modified into an explosion-proof construction without impairment of the accuracy of measurement, thereby permitting its use in an atmosphere having potential fire and/or explosion hazard.

A first leak detection system according to the present invention for gas, steam or the like in a plant yard comprises:

a plurality of sampling modules arranged in the plant yard, wherein each of the sampling modules includes a gas pipe having an interior, a plurality of air inlet tubes attached to the gas pipe in communication with the interior of the gas pipe, and a plurality of air intakes which correspond in number to the number of air inlet tubes, each of the air intakes being connected to a free end of one of the air inlet tubes to collect samples of the surrounding atmosphere;

at least one sensor module connected to each of the sampling modules, for receiving the samples of the atmosphere collected through the sampling modules and having a built-in sensor to detect the concentration of the gas, steam or the like in the atmosphere so received if the gas, steam or the like is leaking from equipment or apparatus in the plant yard;

at least one vacuum pump for normally drawing the samples of the atmosphere which exist in the sampling modules, through the sensor module;

at least one wind direction and velocity indicator for the real-time determination of the direction and velocity of local wind; and a data processor for real-time analysis of wind direction and velocity data obtained from the wind direction and velocity indicator and concentrations of the gas, steam or the like in the atmosphere which have been collected by the sampling modules and detected by the sensor module;

whereby leakage of the gas, steam or the like from the equipment or apparatus in the plant yard over a wide area, can be detected promptly and with a high degree of probability by effectively and constructively using the data of the real-time fluctuations in the wind direction and velocity.

A second leak detection system according to the present invention for gas, steam or the like in a plant yard comprises:

a plurality of sampling modules arranged in the plant yard, each of said sampling modules having a gas pipe whose one end is open, plural air inlet tubes attached to the gas pipe in communication with the interior of the gas pipe, and a like number of air samplers connected to free ends of the respective air inlet tubes to collect samples of the surrounding atmosphere;

at least one sensor module connected to each of the sampling modules at the open ends thereof, for receiving the samples of the atmosphere collected through the sampling modules and having a built-in sensor to detect the concentration of the gas, steam or the like in the atmosphere so received if the gas, steam or the like is leaking from equipment or apparatus in the plant yard;

at least one vacuum pump for normally drawing the samples of the atmosphere which exist in the sampling modules, throught the sensor module;

at least one wind direction and velocity indicator for the real-time determination of the direction and velocity of local wind; and a data processor for real-time analysis of wind direction and velocity data obtained from the wind direction and velocity indicator and concentrations of the gas, steam or the like in the atmosphere which have been collected by the sensor module, and for estimating in real-time fashion the quantity of leakage of the gas, steam or the like, whereby leakage of the gas, steam or the like from the equipment or apparatus in the plant yard over a wide area can be detected promptly and with a high degree of probability.

A third leak detection system according to the present invention for gas, steam or the like in a plant yard comprises:

a plurality of sampling modules arranged in the plant yard for collecting samples of the surrounding atmosphere;

at least one sensor module connected to the sampling modules, for receiving the samples of the atmosphere collected through the sampling modules and having a built-in sensor to detect the concentration of the gas, steam or the like in the atmosphere so received if the gas, steam or the like is leaking from equipment or apparatus in the plant yard;

at least one vacuum pump for normally drawing the samples of the atmosphere which exist in the sampling modules, through the sensor module;

at least one wind direction and velocity indicator for the real-time determination of the direction and velocity of local wind; and a data processor for the real-time analysis of wind direction and velocity data obtained from the wind direction and velocity indicator upon discovery of leakage of the gas, steam or the like and concentrations of the gas, steam or the like in the atmosphere which have been collected by the respective sampling modules as detected by the sensor module;

whereby the point of leakage of the gas, steam or the like is estimated by using real-time fluctuations of the wind direction and velocity data and fluctuations in the concentrations of the gas, steam or the like in the atmosphere collected by the respective sampling modules, the latter fluctuations being caused by the former fluctuations; and the quantity of the leakage of the gas, steam or the like is estimated in a real time fashion.

A first method according to this invention for the determination of the direction and velocity of wind comprises the steps of:

arranging an anemometer element between two shielding plates extending in a substantially parallel and opposing relationship;

allowing the anemometer element and the two shielding plates to rotate as an integral unit about an axis parallel to the anemometer element;

analyzing data of wind velocities measured by the anemometer element, said data corresponding to resulting angles of rotation and determining the direction and velocity of local wind adjacent the anemometer element.

A first wind direction and velocity indicator according to the present invention comprises:

two shielding plates arranged in a substantially parallel and opposing relationship so that a wind inlet and a wind outlet opposite the wind inlet are formed;

an anemometer element disposed between the two shielding plates so that the anemometer element is directed toward the wind inlet;

a motor for rotating the shielding plates and anemometer element as an integral unit about an axis located between the two shielding plates and substantially parallel to the two shielding plates and the wind inlet; and a processor for analyzing angles of rotation of the anemometer element and corresponding data of wind velocities measured by the anemometer element, and thereafter determining the direction and velocity of local wind adjacent the anemometer element.

A second method according to the present invention for the determination of the direction of wind comprises the steps of:

determining in advance the relationship between the angle which is formed between the direction of wind against a first anemometer element arranged inside a natural-draft instrument having a wind inlet and a wind outlet and the direction of natural wind outside the instrument and the first ratio of the velocity of natural wind indicated by the first anemometer element to the velocity of natural wind indicated by a second anemometer element arranged outside the instrument;

installing the instrument at a place where the determination of the direction of natural wind is desired and installing the second anemometer element outside the instrument; and determining the second ratio of the velocity of wind indicated by the first anemometer element inside the instrument to the velocity of natural wind indicated by the second anemometer element outside the instrument and;

determining the direction of the natural wind from the second ratio and the relationship.

A second anemoscope according to the present invention comprises:

a natural-draft instrument having a wind inlet and a wind outlet and equipped with a first anemometer element thereinside;

a second anemometer provided outside the instrument; and a processor for determining the direction of natural wind from (i) the predetermined relationship between the angle which is formed between the direction of wind against the first anemometer element and the direction of the natural wind outside the instrument and the first ratio of the velocity of the wind indicated by the first anemometer element inside the instrument to the velocity of natural wind indicated by the second anemometer element outside the instrument and (ii) the velocity of wind indicated by the first anemometer element.

A third method according to this invention for the determination of the direction of wind comprises the steps of:

determining in advance the relationships between the angles which are formed between the directions of wind against first anemometer elements arranged respectively in 4–16 compartments formed by dividing the interior of a natural-draft instrument, each of said compartments enclosing one of the first anemometer elements and having a wind inlet and a wind outlet and the direction of natural wind outside the instrument and the first ratios of velocities of wind indicated by the first anemometer elements to the velocity of natural wind indicated by a second anemometer element arranged outside the instrument;

installing the instrument at a place, where the determination of the direction of natural wind is desired and installing the second anemometer element outside the instrument;

determining the second ratios of the velocities of wind indicated by the first anemometer elements inside the instrument to the velocity of natural wind indicated by the second anemometer element outside the instrument, and determining the direction of the natural wind from the second ratios and the relationships.

A third anemoscope according to the present invention comprises:

a cylindrical instrument whose interior is divided into 4–16 compartments having a sectorial transverse cross-section of the same interior angle, said cylindrical-instrument having the same number of wind inlets through the cylindrical wall of the instrument as the compartments at equal angular intervals so that all the wind inlets have the same angle relative to a central axis of the cylindrical instrument, said cylindrical instrument defining in a top or bottom wall thereof a wind outlet through which the interiors of the respective compartments communicate to the outside of the instrument, and said compartments enclosing first anemometer elements at right angles relative to the directions of extensions of the corresponding wind inlets;

a second anemometer element arranged outside the instrument;

a processor for determining the direction of natural wind by determining the relationships between the angles which are formed between the first anemometer elements inside the instrument and a central axis of the instrument and the ratios of the velocities of wind indicated by the first anemometer elements inside the instrument to the velocity of natural wind indicated by the second anemometer element outside the instrument and then analyzing the relationships with respect to all of the first anemometer elements inside the instrument.

A fourth method according to this invention for the determination of the direction and velocity of wind comprises the steps of:

installing a natural-draft instrument at a place where the determination of the direction and velocity of natural wind is desired, said instrument having a wind inlet and a wind outlet, and being internally provided with an anemometer element and having negligibly small internal draft resistance;

continuously measuring the wind velocity by the anemometer element while rotating the instrument; and recording as the velocity of the natural wind the maximum value of the so-measured velocities of wind, and as the direction of natural wind the rotated position of the instrument at which the maximum velocity of natural wind was recorded.

A fourth wind direction and velocity indicator according to the present invention comprises:

a natural-draft instrument having a wind inlet and a wind outlet and internally provided with an anemometer element;

a motor for rotating the instrument; and a processor for continuously monitoring the velocity of wind as measured by the anemometer element while rotating the instrument at a constant speed by the motor, storing the resulting angles of rotation of the instrument and the velocities of the wind so obtained, and recording as the velocity of natural wind the maximum value of the so-measured wind velocities and as the direction of natural wind the rotated position of the instrument at which the maximum velocity of natural wind was recorded.

A fifth method according to the present invention for the determination of the direction of wind comprises the steps of:

installing a natural-draft instrument at a place where the determination of the direction of natural wind is desired, said instrument having a wind inlet and a wind outlet and being internally provided with a first anemometer element, and providing a second anemometer element outside the instrument;

continuously measuring the velocity of wind by both the first and second anemometer elements while rotating the instrument;

determining the ratios of velocities of wind indicated by the first anemometer element to corresponding velocities of natural wind indicated by the second anemometer element; and recording as the direction of the natural wind the rotated position of the instrument at which the maximum value of the ratios was recorded.

A fifth anemoscope according to the present invention comprises:

a natural-draft instrument having a wind inlet and a wind outlet and internally provided with a first anemometer element;

a motor for rotating the instrument;

a second anemometer element provided outside the instrument; and a processor for driving the motor at a constant speed, determining the ratios of velocities of wind indicated by the first anemometer to velocities of natural wind indicated by the second anemometer, and determining as the direction of the natural wind the rotated position of the instrument at which the maximum value of the ratios was recorded.

Plural sampling modules-are arranged around apparatus or equipment in a plant yard. Through the sampling modules samples of the atmosphere surrounding the equipment are drawn by a vacuum pump, whereby the concentration of a substance leaking into the atmosphere and being drawn through the individual sampling modules is detected by corresponding sensor modules. When there is no leakage of gas, steam or the like in the plant yard, all the sensor modules generally indicate zero concentration. If the sensor module connected to any one of the sampling modules detects a concentration higher than 0, this indicates some leakage near that particular sampling module.

In general, there is wind over the plant yard and outside the boundary of the plant yard. Accordingly there is also wind near each point of leakage. The direction and velocity of local wind near the point of leakage are substantially different in many instances from those above the plant yard or those outside the boundary of the plant yard because of influence by obstacles such as many apparatus or equipment in the plant yard. Further, they always vary at certain time intervals in accordance with meteorological fluctuations in wind direction above the plant yard. When plural sampling modules have been installed around apparatus or equipment in the plant yard, for example, in such a manner that the apparatus or equipment are surrounded by the sampling modules, any leakage in the plant yard, if any, can be detected generally by a sensor module connected to at least one of the sampling modules because of fluctuations in wind direction.

Due to such fluctuations in the direction of wind around a point of leakage, the sampling module by which the leakage is detected may change from one to another with time and the detected concentration may correspondingly vary along the passage of time. In some instances, leakage may be detected by more than one sampling module.

With the foregoing in view, a wind direction and velocity indicator is arranged in the vicinity of each sampling module, and data of a concentration from the corresponding sensor module and the direction and velocity of wind from the wind direction and velocity indicator are transmitted to a central data processor. On a graphic screen with all the module sets displayed thereon, an area probably encompassing the point of leakage is indicated at the windward of the wind direction measured by the wind direction and velocity indicator against a sampling module which has detected the leakage (more than one sampling module may detect the leakage). Variations in the area, which is likely to encompass the point of leakage, depending on time-dependent variations of the wind direction are overlapped as time-dependent variations and are traced. A leakage point usually remains at a fixed point and is generally considered not to move suddenly. By conducting a trace in accordance with such processing of information as described above, the area probably encompassing the point of leakage is successively narrowed down in accordance with time-dependent variations in wind direction and velocity, whereby the point of leakage can be specified in 1-2 hours if the leakage is 1 $m^3$ or greater an hour. When the area probably encompassing the point of leakage has been specified practically, time-dependent variations of the concentration measured by the sensor module detecting the leakage and those of the wind direction and the wind velocity data obtained from the wind direction and velocity indicator are taken into parallel analysis so that the quantity of leakage can be calculated because a certain relational expression can be established between these variations as will be described hereinafter. Therefore, time-dependent variations of the quantity of leakage can also be recorded and displayed.

Anemometer elements include, for example, a hot-wire anemometer element which will often be abbreviated merely as "element" in the present specification. A hot-wire anemometer element has a small-diameter wire of a certain metal, which is heated by a very small current at a constant temperature higher by several tens of degrees than the temperature of the surrounding atmosphere. When this element is exposed to natural wind, heat is taken away from the element so that the temperature of the element drops. This decrease of the temperature is proportional to the quantity of heat removed per unit time by the gas to which the element is exposed and, hence, to the quantity of the gas flowing per unit time in a narrow temperature range. It is therefore the principle of measurement by a hot-wire anemometer element that the extent of a temperature drop of the element is taken out as an output by using a corresponding change in electrical conductivity or the like and is hence allowed to indicate the velocity of the wind. The sensitivity of measurement of the velocity of wind according to this principle is excellent, thereby making it possible to achieve high-sensitivity measurement even in the case of wind as gentle as 0.1 m/sec or so. Anemometer elements other than hot-wire anemometer elements, for example, Pitot tubes can also be used as they are commercially available with small and precise specifications in recent years.

No limitation is, therefore, imposed on the type of anemometer element usable in the present invention as long as it can be assembled in "an instrument of the construction that a difference occurs between the direction of external natural wind and that of wind against the internal element as the direction of wind varies" and it can provide high measurement accuracy even for low velocity wind.

As long as the velocity of wind remains constant, the velocity of the wind indicated by the element reaches a maximum when the angle (angle of deviation) $\theta$ between the direction of wind against the element and the direction of natural wind is 0 degree. As the angle of deviation $\theta$ becomes greater, the wind velocity indicated by the element decreases and, when the angle of deviation reaches 90 degrees, the wind velocity indicated by the element reaches a minimum. When an instrument of a small draft resistance construction is used, this maximum wind velocity is substantially the same as the velocity of natural wind. Even when the direction and velocity of natural wind vary in various ways, the relationship between the angle of deviation $\theta$ of the element from the direction of natural wind and the ratio R of the wind velocity indicated by the element to the velocity of natural wind can be represented approximately by a certain curve.

The second method for the determination of the direction of wind makes use of this principle. The relationship between the angle of deviation $\theta$ of the element from the direction of natural wind and the ratio R of a wind velocity indicated by the element to the velocity of natural wind is determined in advance, and the direction of natural wind is then determined based on both the velocity of wind indicated by the element in an actual measurement and the relationship described above.

When an instrument composed of two parallel plates is used as an instrument of simple construction, each wind velocity u' indicated by an element assembled in the instrument can be expressed approximately by the following formula when $\theta$ ranges from 0 degree to 90 degrees:

$$u' = u\cos\theta$$

where $\theta$ is the angle of deviation of the element from the direction of natural wind and u is the velocity of the natural wind.

It is therefore easy to determine the direction of wind by calculation if, in the above case, u' is determined by the element inside the instrument and u is determined by an element provided outside the instrument. For $\theta$ in the range of from 90 degrees to 180 degrees, the above relational expression becomes $u' = -u\cos\theta$. Since there is an angle indicating the same u' in the range of from 0 degree to 90 degrees, the above calculation method cannot distinguish the direction of wind at that angle. To overcome this problem, check blades or shields are provided in the air passage, which is defined between the parallel plates, on either the upstream or downstream side relative to the element so that wind velocities at $\theta$s in the range of from 90 degrees to 180 degrees can be brought to zero.

With the above-described method which makes use of an instrument with one element assembled therein, it is difficult however to determine the direction of wind when the angle of deviation $\theta$ from the direction of natural wind exceeds 90 degrees. Further, even at the same angle of deviation $\theta$, it is impossible to distinguish whether the direction of wind is leftward or rightward.

The relationship between the angle of deviation $\theta$ and the ratio R of a wind velocity indicated by the element to the velocity of natural wind will now be discussed. It is known that as the angle of deviation $\theta$ becomes greater in the range of 0° to 180°, the degree of a variation in the ratio R of the wind velocity indicated by the element to the velocity of natural wind decreases and, when the angle of deviation $\theta$ exceeds 45° in particular, the degree of a variation in the ratio R suddenly becomes small. When the angle of deviation $\theta$ is determined by first finding out the ratio R, the direction of wind can be determined more precisely as $\theta$ is closer to 0°. The determined direction of wind, therefore, becomes more precise as the angle of deviation $\theta$ of each element is made smaller by increasing the number of elements in each instrument. Hence, 4–16 elements are assembled in each instrument in the third method for the determination of the direction of wind. The angles of deviation $\theta$ of these elements to the direction of natural wind, said elements being attached in different directions, are different from one another so that they indicate different wind directions. The ratios R of wind velocities indicated by the respective elements, respectively, to the velocity of natural wind, therefore, are different from one another. According to the present method, with respect to some wind velocities, the relationship (simultaneous equations) of the ratios R of wind velocities indicated by each element to the velocity of natural wind with variations in the angle of deviation $\theta$ of the element in the instrument to the direction of natural wind is determined in advance, and the direction of natural wind is then determined from such relationships relating to the respective elements and the ratios R of wind velocities indicated by the respective elements to the velocity of the natural wind. In extreme cases, the arrangement of 16 elements in an instrument makes it possible to perform approximate measurement of up to 16 directions without simultaneous equations provided that the direction of arrangement of the element indicating the maximum ratio R is known.

Further, if an instrument of a symmetrical construction such that the arrangement of elements and the construction of a wind passage around each element are each symmetrical at a given angle relative to a vertical central axis of the instrument is employed, the relationship between the angle of deviation $\theta$ of each element inside the instrument to the direction of natural wind and the ratio R of a wind velocity indicated by the element to the velocity of natural wind is substantially the same irrespective of the element. If the relationship between the ratio R of each wind velocity indicated by a representative element in the instrument to the velocity of natural wind and the angle of deviation $\theta$ of the direction of wind against the element to the direction of the natural wind is determined in advance with respect to several wind velocities, the same equations except that the angle of deviation $\theta$ is different by predetermined angles, respectively, can be applied equally to the other elements.

For a single wind direction, the direction of wind against an element inside an instrument continuously varies as the instrument rotates. When the angular velocity of the instrument is represented by $\omega$ (degrees/minute), the direction of wind against the element at a time t (minutes) from a base time can be expressed by a value which is obtained by adding $\omega t$ to the direction of wind against the element at a base time (hereinafter abbreviated simply as "base direction"). Since the wind velocity indicated by the element reaches a maximum when the angle of deviation $\theta$ of the element inside the instrument is 0 degree, the time at which the maximum wind velocity is indicated is the time at which the direction of wind and that of wind against the element have coincided, if the wind velocity is constant. Representing the base direction by $\theta_o$ (degree), the wind direction at this time can be expressed by adding to the base direction the product of the angular velocity $\omega$ and the time t elapsed until that time from the base time, namely, by $\theta_o + \omega t$. This is the determined wind direction. Where the instrument has a construction such that the draft resistance inside the instrument can be ignored, the wind velocity indicated by the element at this time can be used directly as the determined wind velocity. This is the principle of the fourth method for the determination of the direction and velocity of wind.

If an additional element is provided outside the instrument to measure the velocity of natural wind, and the ratio R of the velocity of wind against each element inside the instrument to the velocity of the natural wind can be known, the direction of wind against the element when the ratio R has reached a maximum is the determined wind direction. This direction can be determined by a similar calculation method to that described above. This is the fifth method of the present invention for the determination of the direction of wind. Determination of the velocity of wind can be precisely conducted in this case because the ratio of the velocity of wind against the element to the velocity of natural wind can be continuously calculated even when the wind velocity varies during measurement.

As has been described above, the present invention has the following advantages.

Plural sampling modules and wind direction and velocity indicators are arranged around apparatus or equipment in a plant yard. Samples of the atmosphere around the apparatus or equipment are drawn through the sampling modules, and the concentration of a substance leaked into the atmosphere drawn through each sampling module is detected by a sensor module. At the same time, the direction and velocity of wind in the plant yard are determined. Leakage of gas, steam or the like in the plant yard can, therefore, be detected in a most economical manner, reliably and with a high probability.

The present invention can provide a highly reliable system for the detection of the leakage of gas, steam or the like by analyzing and processing concentrations which have been detected by individual sampling modules and data from wind direction and velocity indicators and then estimating the point and quantity of leakage.

The direction and velocity of wind can be determined by the combination of simple anemometer elements such as hot-wire anemometer elements, simple instruments and a simple processor (microcomputer) so that, compared to conventional systems, more economical systems can be provided. These systems can, therefore, be used at low cost for the determination of the direction and velocity of wind for the environmental assessment in a factory, office or the like, especially for the prediction of the state of diffusion of noxious gas, steam or the like leaking and also for the precise measurement of low velocity wind to estimate the point of leakage.

BRIEF DESCRIPTION OF THE DRAWINGS

The above and other objects, features and advantages of the present invention will become apparent from the following description and the appended claims, taken in conjunction with the accompanying drawings, in which:

FIG. 5 is a graph showing simulation results (relationship between the range of fluctuations in wind direction and the expected probability of detection) at a plant yard shown in FIG. 1;

DETAILED DESCRIPTION OF THE INVENTION AND PREFERRED EMBODIMENTS

The preferred embodiments of the present invention will next be described with reference to the accompanying drawings. It should, however, be borne in mind that the present invention is not limited to or by the following examples.

Figure 1:
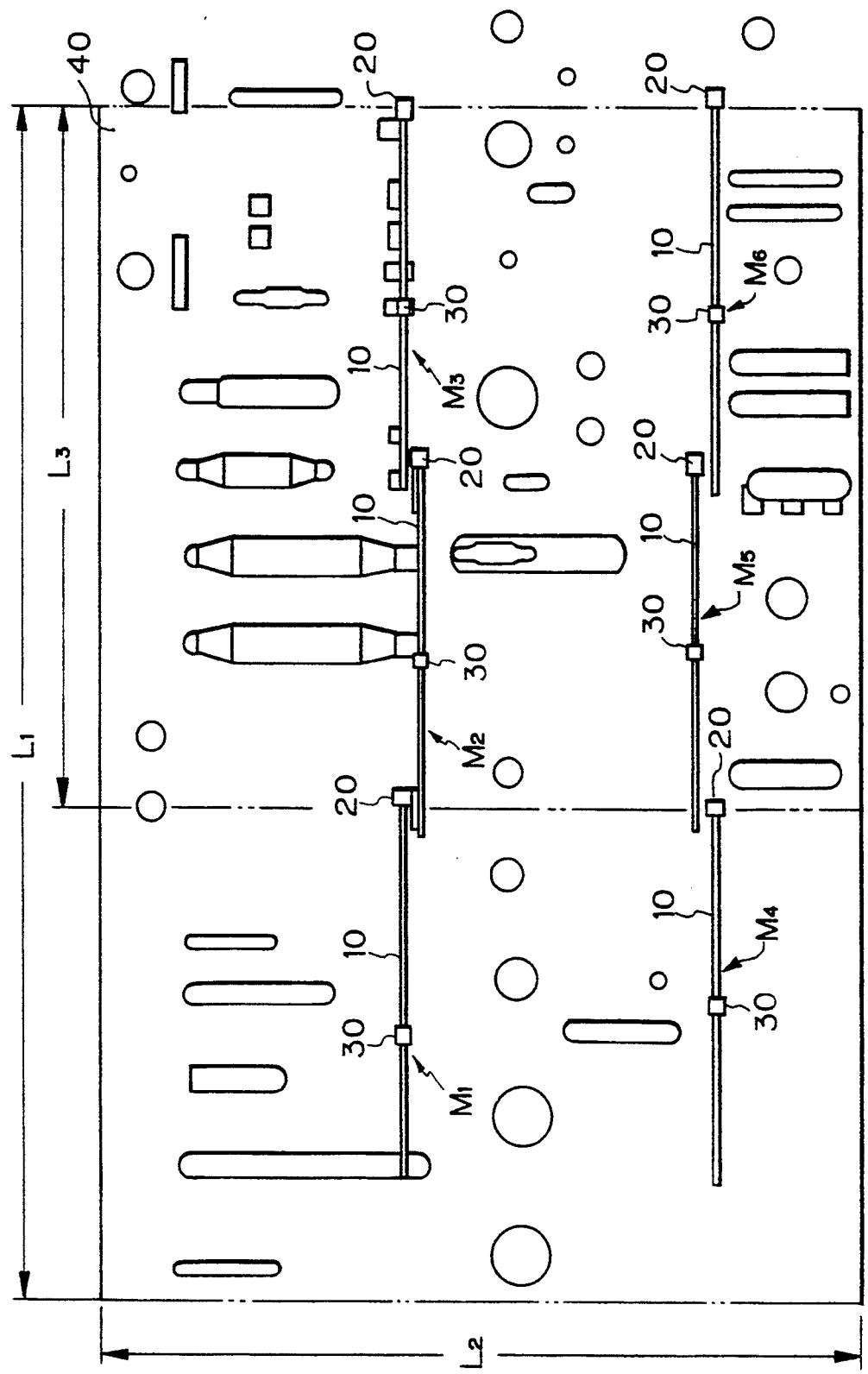
FIG. 1 is a plan view of a plant yard to which a leakage detection system according to one embodiment of this invention has been applied.

The embodiment of FIGS. 1 through 5 has been applied to a liquefied ethylene production plant. As is illustrated in FIG. 1, six module sets $M_1$, $M_2$, $M_3$, $M_4$, $M_5$ and $M_6$, each of which is composed of a sampling module 10, a sensor module 20, and a wind direction and velocity indicator 30 arranged 3 sets by 3 sets in parallel in a plant yard 40 of $L_1 \times L_2 = 60$ m $\times$ 40 m.

Figure 2:
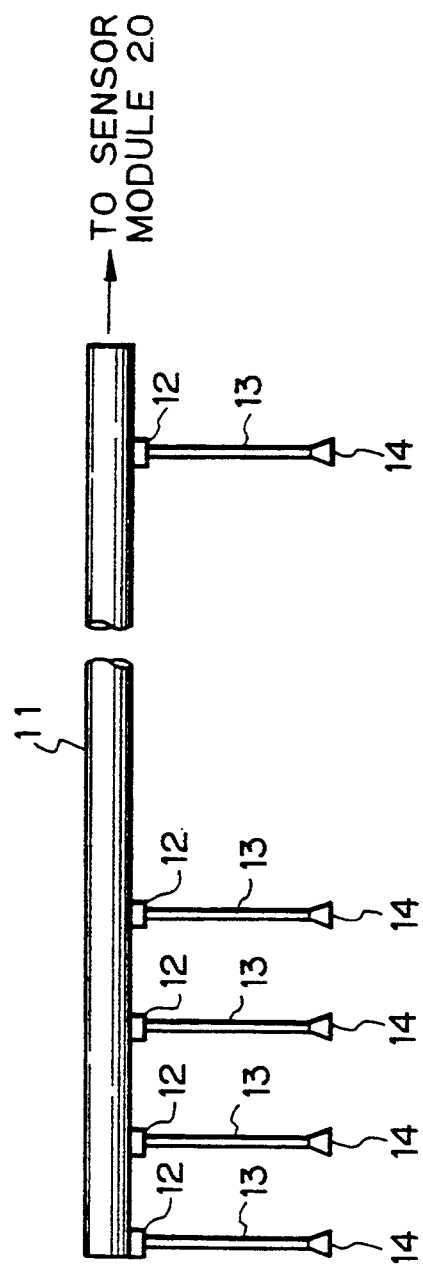
FIG. 2 is a side view of a sampling module 10.

Each sampling module 10 is placed at a height 3–5 m above the ground. As is depicted in FIG. 2, the sampling module 10 is composed of a gas pipe 11 having a length of 20 m, closed at one end and open at the other end, ten unions 12 secured at intervals of 2 m on a peripheral wall of the gas pipe 11, air inlet tubes 13 opening at both ends thereof and connected at one end thereof to the respective unions 12 in such a way that air inlet tubes 13 communicate to the interior of the gas pipe 11, and conical air intakes 14 connected to the other ends of the respective air inlet tubes 13 and having perforated discs at the free ends thereof to prevent penetration of rain water. The open end of the gas pipe 11 is connected to a vacuum pump (not shown) via the sensor module 20. The vacuum pump may be connected to two or more sampling modules 10 to draw samples of the atmosphere therethrough. Although these sampling modules 10 are placed at the height 3–5 m above the ground at various places in the plant yard 40, they may be suitably placed at a different height depending on the state of the plant yard 40. Further, the sampling modules 10 are not necessarily limited to the construction illustrated in FIG. 2. Any modules can be used as long as they can efficiently collect samples of the atmosphere from numerous points in a three-dimensional open space and can guide the samples to their corresponding sensor module or modules. For example, pipes having numerous holes can be employed.

Figure 3:
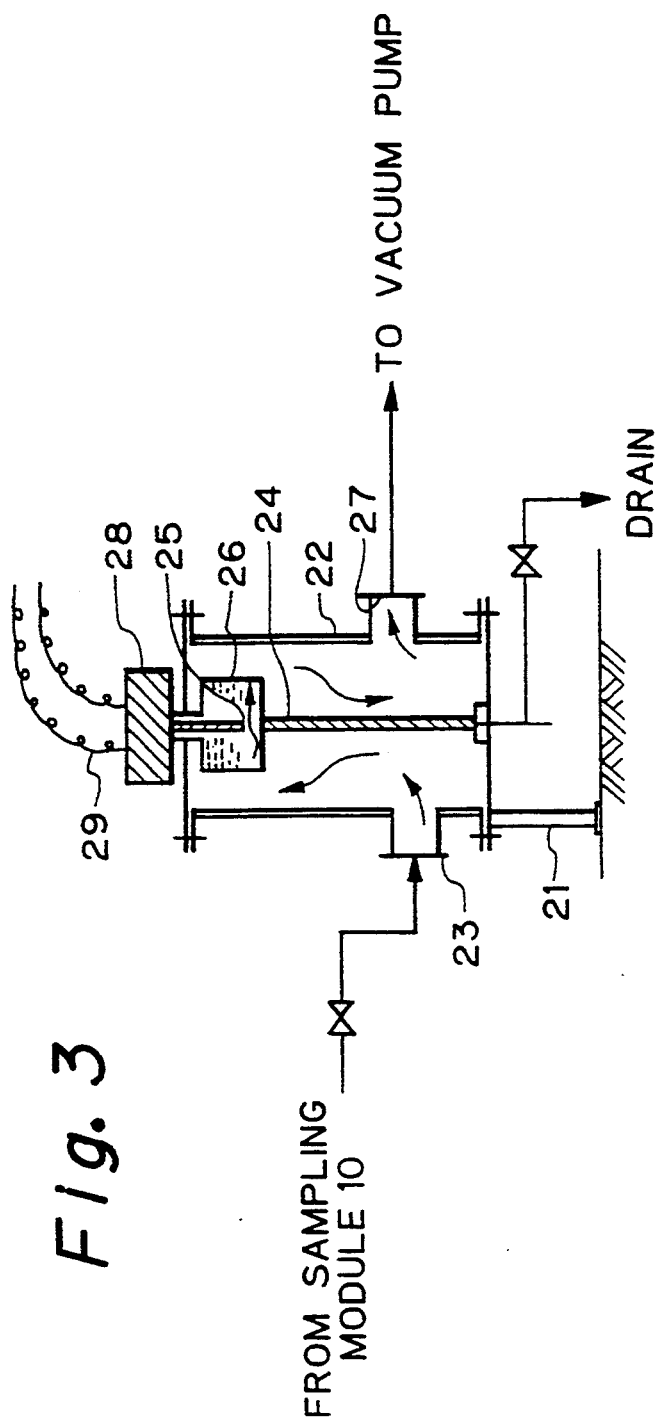
FIG. 3 is a simplified cross-sectional view of a sensor module 20, showing the internal construction thereof.

Each sensor module 20 is, as shown in FIG. 3, arranged on the ground by means of posts 21 and comprises a cylindrical casing 22, an air inlet nozzle 23 for introducing into the casing 22 air samples collected by the associated sampling module 10, a baffle plate 24 dividing the casing 22 into halves, a gas sensor 25 provided above the baffle plate 24, a perforated cylindrical plate 26 surrounding the gas sensor 25, a sample air outlet nozzle 27 adapted to discharge air samples therethrough subsequent to their passage through the perforated plate 26, said air outlet nozzle 27 being connected to a vacuum pump, a terminal box 28 disposed on a top part of the casing 22 and connected to the gas sensor 25, and signal lines 29.

Each air sample collected by the sampling module 10 is guided through the sample air inlet nozzle 23 into the casing 22 and enters one half section of the casing 22. The air sample ascends in the space defined by the baffle plate 24 and then enters the interior of the gas sensor 25 through a plurality of holes opened in a cylindrical side wall of the perforated plate 26. The air sample flows further past the gas sensor 25 and then descends through the other half section of the casing 22. The air sample is drawn by the vacuum pump through the sample air outlet nozzle 27 and is then released into the atmosphere through an outlet of the vacuum pump. In this case, an ethylene gas sensor is provided as the gas sensor 25. When the present invention is applied to a plant, sensors for a substance handled in the plant are generally used. Sensors of the most preferable type at the present stage are semiconductor sensors, and a variety of semiconductor sensors are available on the market. Although higher detection sensitivity is preferred, the ability to detect levels of 5–10 ppm is desired. Detection signals are fed to a data processor (not shown) via the signal lines 29.

One sensor module 20 is connected to one sampling module 10 in the present embodiment. It is, however, possible to arrange a plurality of sampling modules 10 in association with a single sensor module 20 and to switch over the sensor module 20 in a time-divided fashion to sequentially connect it to the respective sampling modules 10.

Figure 4B:
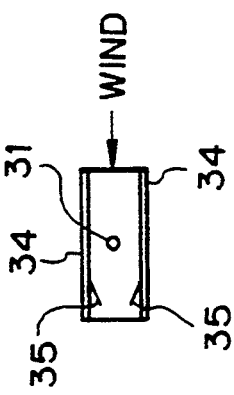
FIG. 4A is a side view of a wind direction and velocity indicator 30 and FIG. 4B is a plan view of the indicator 30.
Figure 4A:
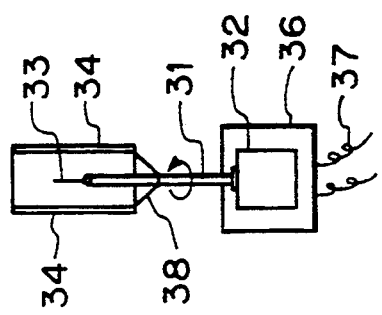

Each wind direction and velocity indicator 30 is arranged as illustrated in FIG. 4. The indicator 30 includes a motor 32 with a drive shaft 31 extending in a substantially vertical direction, driven at a constant speed of about 120° per minute, a hot-wire anemometer element 33 held on the drive shaft 31 of the motor 32, two shielding plates 34 having substantially the same shape and dimensions and fixed on the drive shaft 31 by shielding-plate-fixing arms 38 so that the shielding plates 34 extend parallel to the drive shaft 31 and rotate together with the drive shaft 31 while facing each other and flanking the drive shaft 31 with a hot-wire anemometers element 33 therebetween, check vanes 35 attached to the inner walls of the shielding plates 34 at locations adjacent one of the openings, which are defined between both shielding plates 34 extend parallel to the drive shaft 31, so that a flow passage for samples of the atmosphere flowing between both shielding plates 34 is gradually constricted toward said opening, and a signal processor 36 for determining the direction and velocity of local wind in the vicinity of the hot-wire anemometer element 33 by analyzing data of wind velocities corresponding to rotated angles of the shielding plates 34 and measured by the hot-wire anemometer element 33. The measurement results processed by the signal processor 36 are delivered to an unillustrated data processor through signal lines 37.

The signal intensities I of output signals from the wind direction and velocity indicator 30 can be diagrammatically expressed in the form of a curve which resembles the relational expression, $I = u\cos\theta$, where $\theta$ is the angle between the shielding plates 34 and the direction of the local wind and u is the velocity of the local wind. In the case of an angle of rotation different over 180° from the direction of the local wind, the local wind velocity u is measured low owing to the function of the check vanes 35 so that the intensity I of the corresponding output signal is low. It is therefore possible to distinguish the direction of forward wind from that of backward wind. Data processing of variations of the signal intensity I with the passage of time, therefore, permits simultaneous determination of the direction and velocity of local wind and further recording of their real-time variations. The check vanes 35 are provided to permit the distinction of the direction of forward wind from that of backward wind flowing in a direction opposite to the forward wind. Any means can be used insofar as they have the same effects as the check vanes, namely, they can change the wind velocity u to be measured. The indicator 30 is accordingly not limited to the use of such check vanes. For example, the shielding plates 34 can be bent inwardly on the side of the discharge opening for samples of the atmosphere so that the flow passage defined between the shielding plates 34 is gradually constricted toward the discharge opening.

The wind direction and velocity indicators 30 are not required when information on the extent of leakage is not particularly required. To apply the present invention to the discovery of only leakage of gas, steam or the like in the plant yard and to find out the leakage of gas, steam or the like in the plant yard more promptly with a higher degree of probability without influence such as noise by external disturbance while effectively and positively utilizing time-dependent variations in the direction and velocity of wind, it is necessary to suitably arrange only sampling modules 10, sensor modules 20 and vacuum pumps in the plant yard. For this reason alone, the significance of this invention is great. By the combination of the constructive utilization of fluctuations in the direction and velocity of wind due to natural conditions, which idea is not previously utilized and the arrangement of sampling modules in a plant, which differs from discrete arrangement of independent detectors, unexpected, accidental leakage of gas can be discovered promptly and without failure. Such a method as to utilize time-dependent variations in the direction and the velocity of wind can also be employed in a narrow and small area. If it is desired to estimate the point of leakage of gas and time-dependent changes in the quantity of leaking gas without relying upon human effort, it is only necessary to arrange wind direction and velocity indicators in addition to the system described above. Further, the sampling modules 10 can be arranged as desired, depending on the importance of each plant yard. A simulation makes it possible to determine to what extent the capacity to detect leakage changes depending on the manner of the arrangement. From the results of such a simulation, the present system can be designed as desired.

The concentrations of gas, steam or the like in the individual samples of the atmosphere collected through the respective sampling modules 10, said concentrations having been determined by the corresponding sensor modules 20, as well as the data on the directions and velocities of wind determined by the respective wind direction and velocity indicators 30 are transmitted to the data processor. On a graphic screen capable of displaying all the module sets $M_1$–$M_6$ thereon, the area probably encompassing the point of leakage is drawn for the sampling module or modules 10 which detected the leakage, on an upstream side with respect to the direction of wind measured by the wind direction and velocity indicators 30, and the area probably encompassing the point of leakage is then synthesized in accordance with time-dependent variations in the direction of wind. By tracing the time-dependent variations in the area possibly including the point of leakage, the point of leakage can be estimated. When the area possibly including the point of leakage has been substantially determined, the quantity of leakage can be calculated from the concentration measured by the sensor module 20 detecting the leakage and the wind velocity obtained from the corresponding wind direction and velocity indicator 30.

Next, the method of simulation referred to above will be outlined.

In general, diffusion of gas into the atmosphere has been reported by many researchers. According to Sakagami's report [Jiro Sakagami: Koatsu Gas (High-Pressure Gas), 19(4), 6 (1982)], when gas is caused to diffuse by wind blowing at a velocity u(m/sec) from a point source at a height H(m) from the ground at the rate of $Q(m^3/sec)$, the concentration of the gas $C(m^3/m^3)$ at a point with coordinates (x, y, z) can be expressed by the following formula, x being the distance (m) from the point source in the leeward direction, i.e., x-axis, y being the distance (m) from the x-axis and z being the height (m) from the ground;

$$C=(Q/u)\{\exp(-y^2/A)/(\pi A)^{\frac{1}{2}}\}(1/B)$$

$$\times \exp\{-(H+z)/B\}I_0\{2\times(Hz)^{\frac{1}{2}}/B\}$$

wherein $I_o$ indicates a modified Bessel function of the first kind of order O.

To simplify the explanation, only a height range several meters above the ground will be dealt with. Height directions in this range are averaged, and the term containing the height H and z is indicated by $\alpha$, namely:

$$a=\exp\{-(H+Z)/B\}I_0\{2\times(Hz)^{\frac{1}{2}}/B\}$$

If this $\alpha$ can be empirically determined by an average, $$C[\text{ppm}]=a(10^6\times Q/u)\{(1B)/(\pi A)^{\frac{1}{2}}\}\exp(-y^2/A)$$

$$A[m^2]=q_A[\ _A X+\exp(-\ _A X)-1]$$

$$B[m]=q_B[\ _B X+\exp(-\ _B X)-1],$$

In the above formula, $_A[1/m]$, $_B[1/m]$, $q_A[m^2]$, $q_B[m]$ are given by the stability of the atmosphere and the height H (the height of the leakage point) in the form of a table. Accordingly, the isoconcentration curve from the point of leakage can be simplified as:

$$y=\pm[A\ln\{1/(D_{(x)}C)\}]^{\frac{1}{2}}$$

where
y: radius perpendicular to the direction of wind, and
$D_{(x)}$: $(10^{-6}u/Q)\{B(\pi A)^{\frac{1}{2}}\}(1/\alpha)$ Needless to say, it is not always necessary to average the height directions to empirically determine $\alpha$, and it is thereby possible to conduct a three-dimensional simulation including the height z.

The simulation uses random numbers, i.e., it is of the type generally called the "Monte Carlo simulation". Such a simulation is simple when an average is used for the height direction as described above. When the probability of successful detection can be determined by inputting as uniform random numbers the maximum quantity of leaked gas, the point (x,y) of leakage, the maximum wind velocity, the wind direction and the stability of the atmosphere, calculating the aforementioned isoconcentration curve for the respective concentrations C (ppm) and repeatedly testing for the existence or absence of any module set detectable within the radius y, this probability can be considered to be the expected probability of detection with respect to one proposal for the arrangement of the module sets. Here, it is to be noted that the direction and velocity of wind are not constant but vary over time. Hence, the velocity of wind is fixed at the average of wind velocities within a predetermined period of time, and the usual range of fluctuations is inputted as a standard deviation above and below the average to change the wind velocity. According to a substantiation experiment conducted to substantiate the advantages of the present invention, these fluctuations may be considered to be a normal distribution whose standard deviation is about $\frac{1}{3}$ of the average. In a plant yard, the direction of local wind fluctuates not only due to variations in weather but also due to the influence of various obstacles. Fluctuations within a certain period of time, however, show a normal distribution having a range of angular variations of a certain standard deviation in the average wind direction. In a substantiation experiment conducted to substantiate the advantages of the present invention, the standard deviation of the range of these angular variations within 3 minutes is about 44° and this value remained substantially the same even over several hours. In an analysis by such a simulation, it is therefore only necessary to consider variations in wind direction up to twice the standard deviation, namely, up to $\pm 88°$ after setting the central wind direction axis (equivalent to an average wind direction) by uniform random numbers in a test.

To substantiate the advantages of the present invention, a substantiation test was next conducted at an actual plant yard. The test was performed within the right-hand half of the plant yard 40 illustrated in FIG. 1, namely, inside the area of $L_2 \times L_3 = 40$ m $\times$ 40 m.

As is illustrated in FIG. 1, the four module sets $M_2$, $M_3$, $M_5$, $M_6$ are arranged in this area. The detection performance of the system according to this invention was tested by dividing this area into 64 sections and causing ethylene to leak out in particular sections. The experiment was conducted many times at different hours of the day. The quantity of gas leakage and the height of leakage were set at 1 m$^3$ or 3 m$^3$ per hour and at 1 m or 2 m above the ground, respectively, and semiconductor sensors were employed as the sensor modules 20. The sensitivity of these sensors to ethylene gas was 5–10 ppm. Gas sensors of this type are now readily available as general commercial products.

As a result of the experiment, the leakage detection probability was found to be 79.7%, the standard deviation 13.2% and the range of scattering of the data 62.5–100%, all as averages of data collected through repeated experimentation. In order to compare these results with those of the above simulation, calculation was conducted by substituting the conditions for the present substantive experiment for the trial input conditions for the above simulation. It was found that when fluctuations in the wind direction within a predetermined time period are $\pm 80°$, the expected probability of detection is 75%, which is very consistent with the results of the present substantive experiment.

With respect to each arrangement pattern of module sets, it is possible to predict its results by a simulation on the basis of the above results. It is therefore possible to design the system of this invention in accordance with the nature (the scale, the properties of a substance handled, the manner of handling, etc.) of a plant yard to which the system is to be applied.

The area of the plant yard to which the system of this invention was applied was enlarged to cover the entire area of the plant yard shown in FIG. 1, and a simulation was conducted choosing leaking conditions entirely at random. The results of the simulation are shown in FIG. 5. If the sensitivity of the sensors employed in the sensor modules 20 are of the 5–10 ppm level, the curve for 25–50 ppm can be used in the diagram. If the range of fluctuations in the direction of wind is $\pm 88°$, the expected probability of detection is 90–100%. When detectors are arranged along the boundary of a plant yard at intervals of 20 m with one detector in accordance with the statutory rule, the expected probability of detection estimated by such a simulation is only 5%. This has also been confirmed by the substantiation test described above.

In general, the area in which leakage of gas can be detected by a single detector under the conditions of constant wind direction, constant wind velocity and constant leakage rate is of an elongated elliptical shape in a height-wise cross-section of the arranged detector. On the other hand, in the case of a single sampling module equipped with a sensor module of the same sensitivity as the single detector, the detectable area is somewhat rectangular in shape and extends in parallel with the module. Even if leakage is once detected by a single detector, the location of the detectable area may soon shift outside the range of the detector if the direction of wind changes. In contrast, the use of the sampling module makes it possible to continuously output a detection signal. In the case of a single detector, the output signal is intermittent and cannot be distinguished from external noise. The present invention makes it possible to substantially increase the signal/noise ratio so that leakage of gas can be determined without failure. Moreover, in the present invention, the natural fluctuations in the direction and velocity of wind can effectively be used. If a plurality of modules are deployed, the area in which leakage of gas can be detected by the plurality of modules is in the form of overlapped rectangles due to such fluctuations, and this further increases the signal/noise ratio. In the example diagrammatically illustrated in FIG. 5, such an arrangement results in a detection probability as high as about 5 times that (detection probability: 20%) available for a constant wind direction, namely, a detection probability of nearly 100% can be expected in a state clearly distinguishable from noise.

Advantages of the present embodiment will now be summarized. In the case of leakage of 1 m$^3$ per hour or more, the expected probability of detection of the leakage within several minutes after the occurrence of the leakage is at least 80% when modules are arranged as in FIG. 1. If it is sufficient to detect the leakage in several hours, it is highly likely that a wind direction fluctuation of at least $\pm 90°$ would take place. This makes it possible to expect a detection probability of at least 90%, more specifically close to 100%. The conventional simple method in which detectors are arranged at intervals of 20 m with one detector at each location cannot be expected to contribute significantly to the safety of the plant. The method of this invention has, however, demonstrated that it can improve the safety to a significant extent and can be employed as a highly practical system.

The shape, combination and the like of the module sets in the present invention are not limited to the examples described above. For example, it is possible to employ sampling modules in a ring-shaped, vertical, inclined or other configuration. Advantages available from such configurations are readily inferable without the need for further discussion. It is also at the user's volition to choose the type and sensitivity of sensors for use in sensor modules depending on the kind of the gas to be detected and the leakage level to be detected. Needless to say, the present invention can be used for the detection of leakage of radioactivity at nuclear power stations.

The anemoscope according to the second embodiment of this invention will next be described with reference to FIGS. 6A, 6B and 7.

Disposed in a wind tunnel 51 is an instrument 52, which is composed of two parallel plates 54 with check vanes 55 at rear ends relative to the direction of wind and a hot-wire anemometer element 53 accommodated between the parallel plates 54. Outside the instrument 52, another hot-wire anemometer element 56 is arranged. Provided outside the wind tunnel 51 is a processor 58, which is connected to the hot-wire anemometer elements 53, 56 via cables 57a, 57b to determine the angle of deviation $\theta$ from wind velocities indicated by the two hot-wire anemometer elements 53, 56.

The wind velocity inside the wind tunnel 51 was varied from 0.5 m/sec to 2.0 m/sec, 4.0 m/sec and 10.0 m/sec. At each constant wind velocity, the direction of the instrument 52 was changed in a horizontal plane [i.e., in a plane parallel to the plane of FIG. 6A] so that the angle between the direction of wind against the element 53 and the direction of wind outside the instrument (i.e., "the angle of deviation $\theta$ from the direction of natural wind" as defined above) was changed from 0 degree to 180 degrees. In this manner, velocities indicated by the hot-wire anemometer element 53 were recorded. In addition, the velocity of wind inside the wind tunnel 51 (i.e., "the velocity of natural wind" as defined above) was measured by the hot-wire anemometer element 56. The ratios of the wind velocities recorded before to the velocity of natural wind (i.e., the ratios R to the wind of natural wind as defined above) were then determined.

Figure 9:
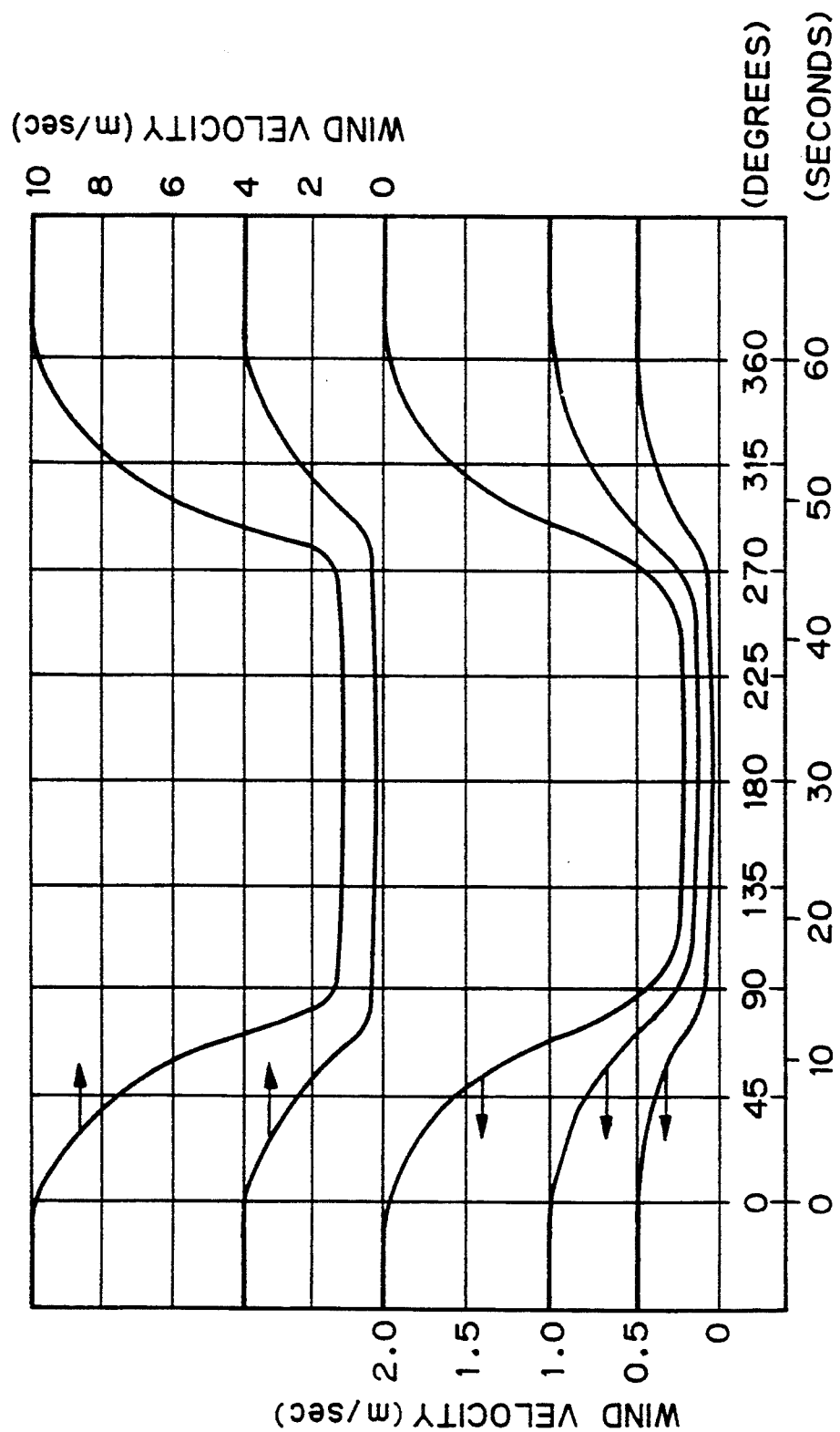
FIG. 9 is a graph showing variations in wind velocity in the third embodiment.

Data of the experiment and averages of ratios R to the velocity of natural wind at various angles of deviation $\theta$ from the direction of natural wind are summarized in Table 1. Further, the relationship between these angles of deviation $\theta$ from the direction of natural wind and the averages of the ratios R to the velocity of natural wind is shown in FIG. 7. Data representing the relationship between the angles of deviation $\theta$ from the direction of natural wind and the averages of the ratios R to the velocity of natural wind, said relationship being shown in FIG. 7, are stored in the processor 58. Wind velocities indicated by the anemometer elements 53, 56, respectively, are inputted to the processor 58. The processor 58 then calculates the ratio R to the velocity of natural wind and, based on the relationship, determines the angle of deviation $\theta$ from the direction of natural wind.

noted that both time and angle are plotted along the axis of abscissas of the graph shown in FIG. 9.

The time required for the above measurement is the time required for a full rotation of the instrument 52, for example, about 1 minute or so.

Figure 10B:
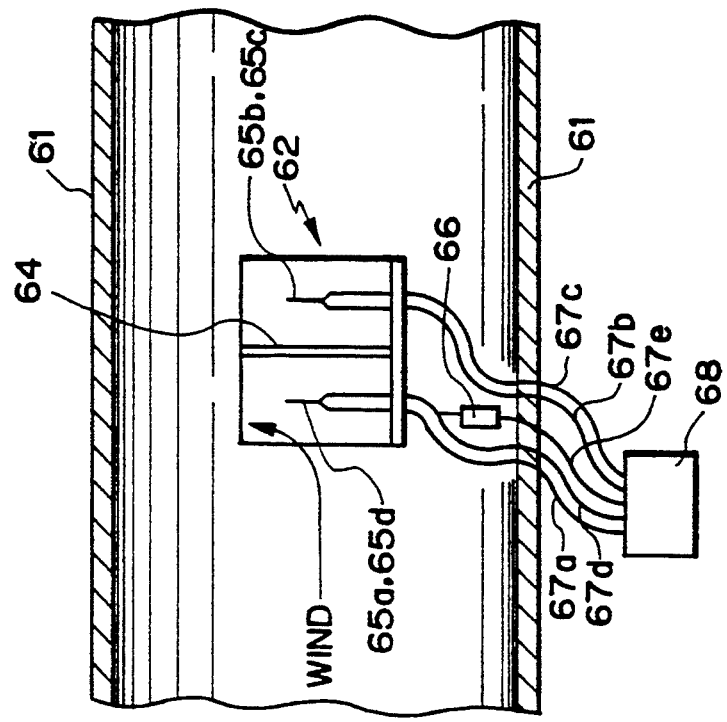
FIG. 10A is a plan view of an anemoscope according to a fourth embodiment of the present invention and FIG. 10B is an elevation of the anemoscope.
Figure 10A:
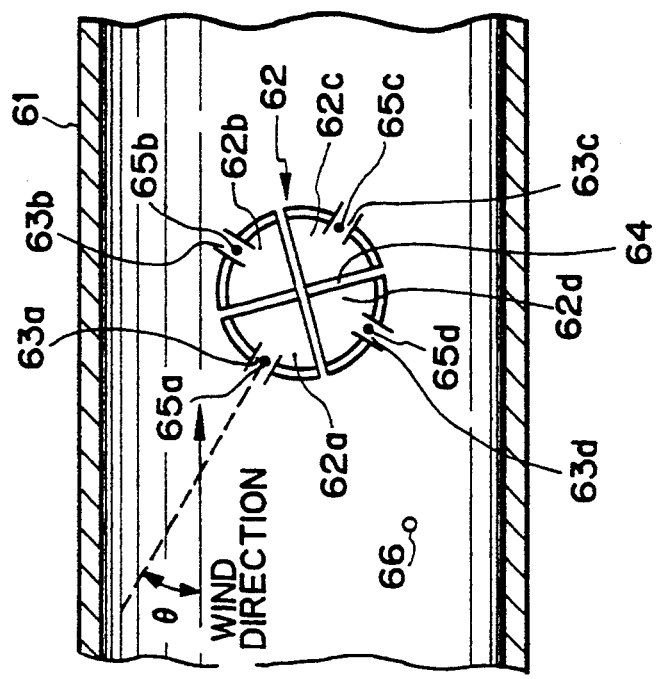
Figure 11:
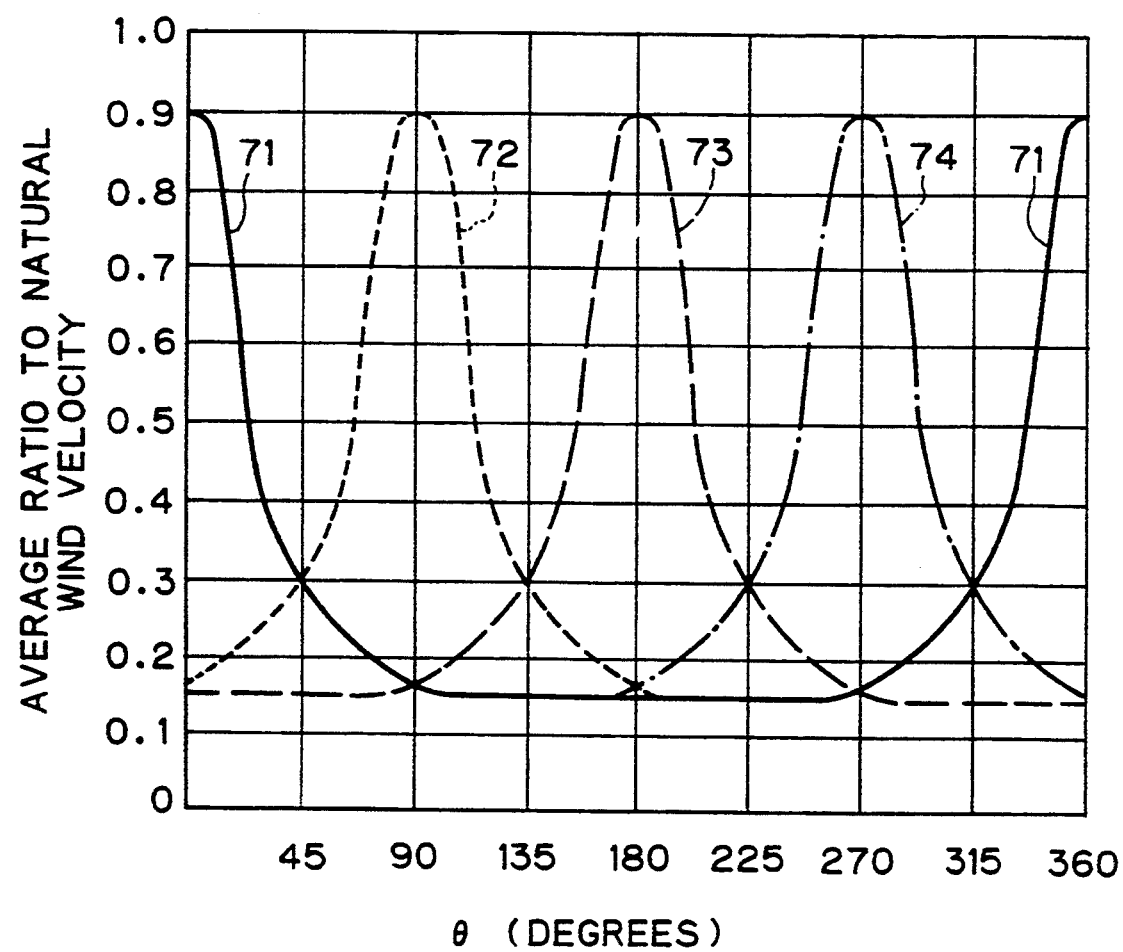
FIG. 11 is a graph showing the average ratio R to natural wind velocity as a function of the angle of deviation $\theta$ from natural wind direction in the fourth embodiment.

The anemoscope according to the fourth embodiment of the present invention will next be described with reference to FIGS. 10A, 10B and 11.

In the fourth embodiment, a cylindrical instrument 62 and a hot-wire anemometer 66 arranged outside the instrument are arranged in a wind tunnel 61. The instrument 62 is divided by a partition 64 into four sectorial sections 62a, 62b, 62c, 62d whose interior angles are all 90 degrees. Formed at equal intervals of 90 degrees through a cylindrical wall are wind inlets 63a, 63b, 63c, 63d which extend toward the central axis of the cylinder. The instrument 62 is open only in the top wall thereof to form a wind outlet. In the respective wind inlets 63a, 63b, 63c, 63d, hot-wire anemometer elements 65a, 65b, 65c, 65d are provided at right angles to the directions along which the wind inlets 63a, 63b, 63c, 63d extend. Provided outside the wind tunnel 61 is a processor 68 which is connected to the respective hot-air anemometer elements 65a, 65b, 65c, 65d via cables 67a, 67b, 67c, 67d, respectively, to determine the direction of natural wind.

The wind velocity was varied from 0.5 m/sec to 2.0

TABLE 1

| Velocity of natural wind (m/sec) | Angle of deviation (degree) | | | | | | | | |
|---|---|---|---|---|---|---|---|---|---|
| | 0.0 | 22.5 | 45.0 | 67.5 | 90.0 | 112.5 | 135.0 | 157.5 | 180.0 |
| | Indicated wind velocities (m/sec) (upper) | | | | | | | | |
| | Ratio R (lower) | | | | | | | | |
| 0.5 | 0.5 | 0.3 | 0.17 | 0.15 | 0.14 | 0.11 | 0.11 | 0.10 | 0.10 |
| | 1.00 | 0.60 | 0.34 | 0.30 | 0.28 | 0.22 | 0.22 | 0.20 | 0.20 |
| 2.0 | 2.0 | 1.1 | 0.60 | 0.55 | 0.45 | 0.35 | 0.30 | 0.25 | 0.30 |
| | 1.00 | 0.55 | 0.30 | 0.28 | 0.23 | 0.18 | 0.15 | 0.13 | 0.15 |
| 4.0 | 3.6 | 2.2 | 1.1 | 0.9 | 0.7 | 0.6 | 0.5 | 0.5 | 0.5 |
| | 0.80 | 0.55 | 0.28 | 0.23 | 0.18 | 0.15 | 0.13 | 0.13 | 0.13 |
| 10.0 | 9.0 | 5.0 | 3.0 | 2.2 | 1.8 | 1.6 | 1.4 | 1.2 | 1.4 |
| | 0.90 | 0.50 | 0.30 | 0.22 | 0.18 | 0.16 | 0.14 | 0.12 | 0.14 |
| Averages of ratio R | 0.95 | 0.55 | 0.30 | 0.26 | 0.22 | 0.18 | 0.16 | 0.15 | 0.16 |

Figure 8B:
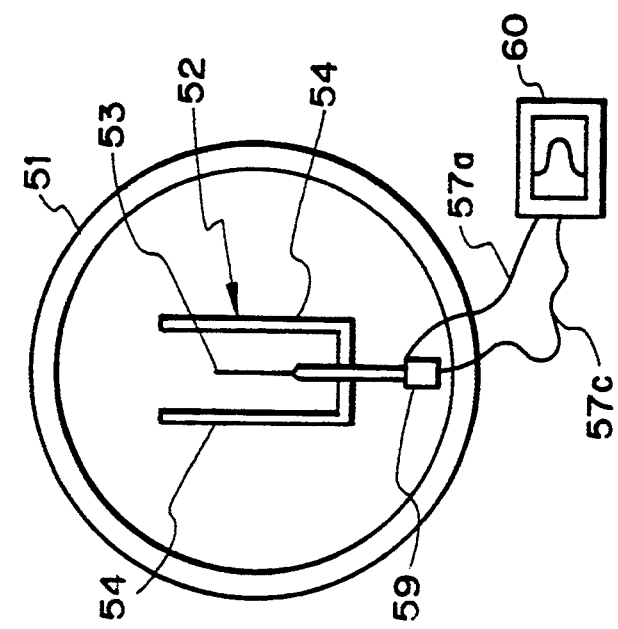
FIG. 8A is a plan view of an instrument for the determination of the direction and velocity of wind according to a third embodiment of this invention and FIG. 8B is an elevation of the instrument.
Figure 8A:
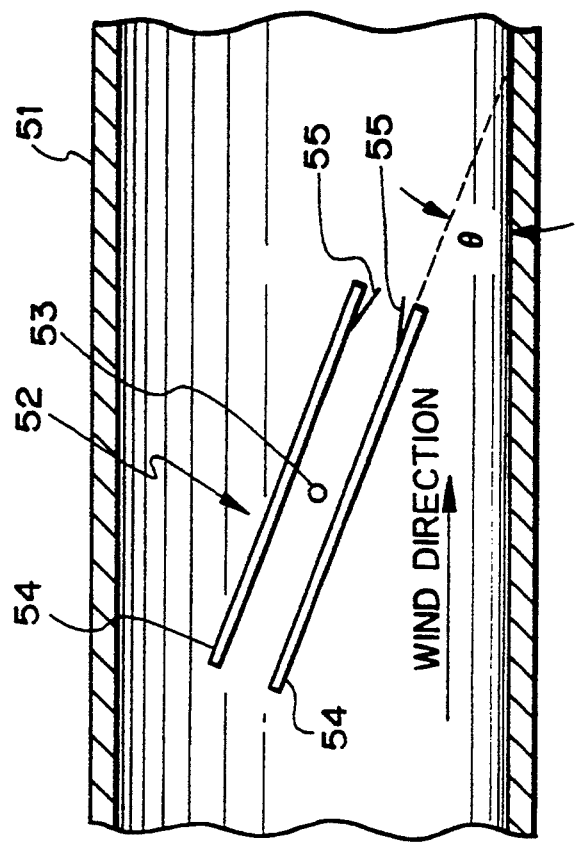

The instrument for the determination of the direction and velocity of wind according to the third embodiment of this invention will now be described with reference to FIGS. 8A, 8B and 9.

Figure 6B:
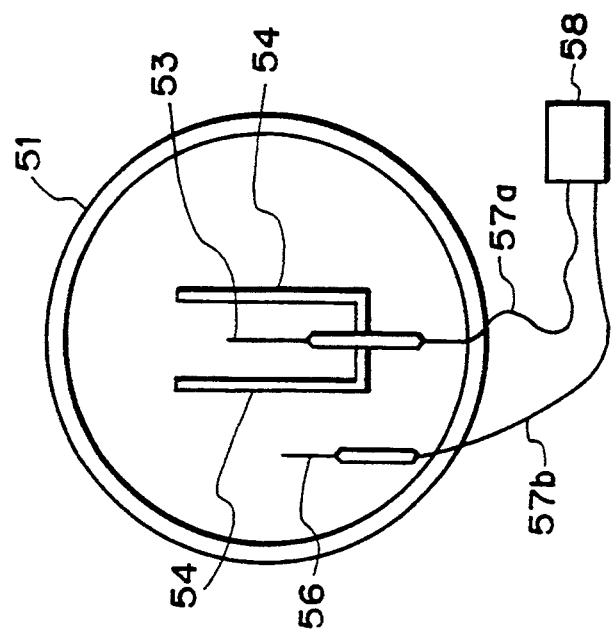
FIG. 6A is a plan view of an anemoscope according to a second embodiment of this invention and FIG. 6B is an elevation of the anemoscope.
Figure 6A:
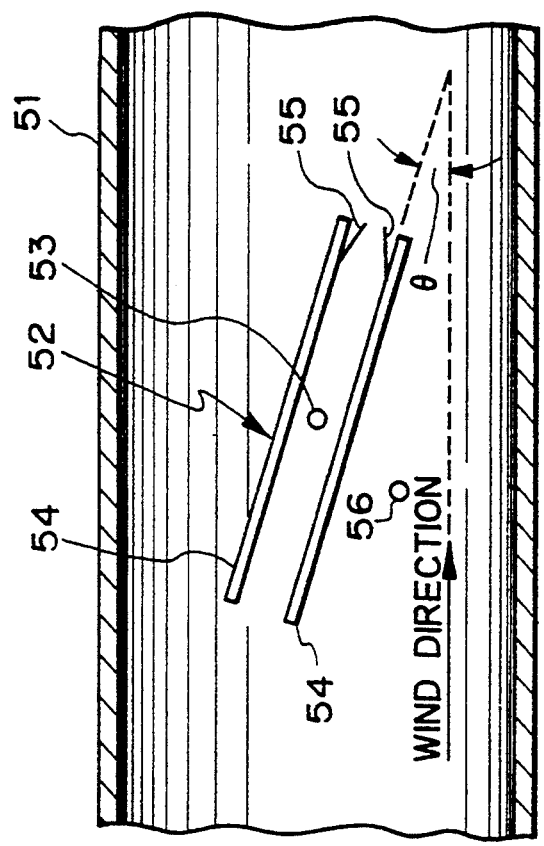
Figure 7:
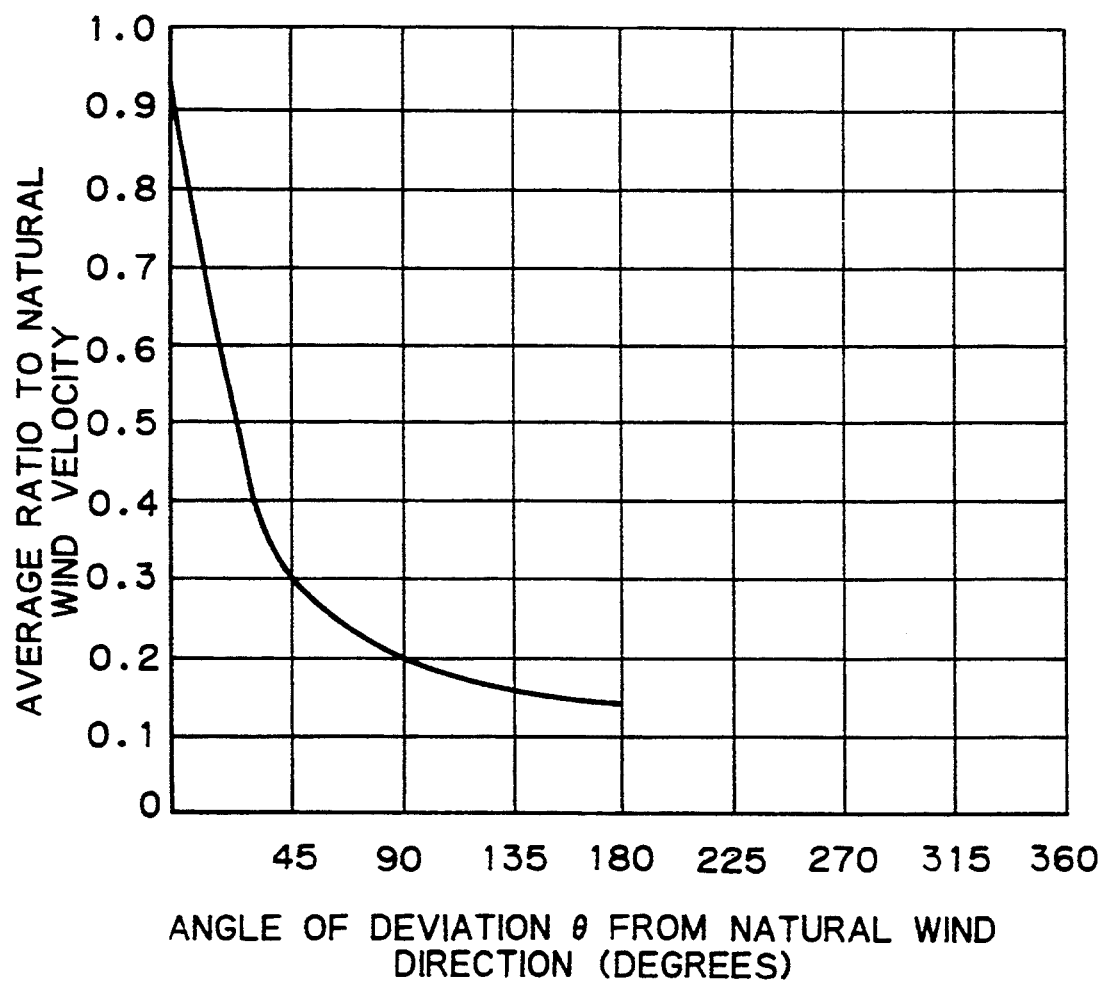
FIG. 7 is a graph showing the average ratio to natural wind velocity as a function of the angle of deviation from natural wind direction in the second embodiment.

This embodiment is different from the second embodiment of FIGS. 6A and 6B in that the hot-wire anemometer element 56 has been omitted, a motor 59 is provided to rotate the instrument 52 and the details of processing by a processor 60 are different from those of the processor 58 of the previous embodiment. The motor 59 is connected to the processor 60 via a cable 57c.

The processor 60 memorizes the maximum value indicated by the hot-wire anemometer 56 during one rotation of the instrument. The maximum value and the angular position of the instrument 52 at the maximum value which are memorized are recorded as the velocity of the natural wind and the direction of the natural wind, respectively.

The wind velocity was varied from 0.5 m/sec to 2.0 m/sec, 4.0 m/sec and 10.0 m/sec inside the wind tunnel 51. At each constant wind velocity, the instrument 52 was rotated at an angular velocity of one revolution per minute (360 degrees/min). Wind velocities indicated by the hot-wire anemometer element 53 during the rotation were continuously recorded in the processor 60, thereby obtaining the results shown in FIG. 9. It is to be m/sec, 4.0 m/sec and 10.0 m/see inside the wind tunnel 61. At each constant wind velocity, the direction of the instrument 62 was changed in a horizontal plane whereby the angle of deviation $\theta$ of the hot-wire anemometer element 65a to the direction of natural wind was changed from 0 degree to 360 degrees. In this manner, velocities indicated by the four hot-wire anemometer elements 65a, 65b, 65c, 65d were recorded. Further, the velocity of natural wind inside the wind tunnel 61 was also measured by the hot-wire anemometer element 66 provided outside the instrument 62, whereby the ratios R of the wind velocities indicated by the respective hot-wire anemometer elements 65a, 65b, 65c, 65d to the velocity of natural wind were determined. The relationship of each angle of deviation $\theta$ from the direction of natural wind and the average of the ratios R to the natural wind velocity from experimental data is diagrammatically depicted in FIG. 11, in which numerals 71, 72, 73 and 74 indicate the averages of wind velocities indicated by the hot-wire anemometer elements 65a, 65b, 65c, 65d to the natural wind velocity, respectively. Angles of deviation from the direction of natural wind are shown taking the hot-wire anemometer element 65a as a base. When the deviation angle of the hot-wire anemometer element 65a is represented by $\theta$ (degrees), the deviation angles of the remaining elements 65b, 65c, 65d are $\theta+90$, $\theta+180$ and $\theta+270$. At the processor 68, ratios $R_1$, $R_2$, $R_3$ and $R_4$ to the natural wind velocity obtained by actual measurement (said ratios corresponding to the hot-wire anemometer elements 65a, 65b, 65c, 65d, respectively) are introduced into four relational expressions between the ratio R to the natural wind and the angles of deviation $\theta$, said relational expressions having been obtained in advance, and the four relational expressions are solved simultaneously to obtain a single angle of deviation $\theta$.

The hot-wire anemometer elements employed in this embodiment have a high degree of measurement accuracy even for low-velocity wind in the range of 0.1 m/sec. When they are assembled in an instrument, the direction of wind in the instrument can be indicated with a high degree of accuracy provided that the velocity of the wind is 0.1 m/sec or higher. The method of this embodiment has made it possible to measure with a high degree of accuracy the direction and velocity of low-velocity wind of approximately 0.5 m/sec, although measurement of the direction and velocity of such low-velocity wind was difficult by any prior art technique.

Further, the hot-wire anemometer element are each made from wire of small-diameter such as a fine metal wire and heated by a small current at a constant temperature several tens of degrees higher than the surrounding temperature. They can therefore be used, as they are, even in areas exposed to potential explosion and/or fire hazard. In the case of fixed instruments such as those of the first and third embodiments, no particular limitation is imposed on their specification even when they are used in such environments. It is ever possible to use rotated instruments such as the instrument 52 of the second embodiment, by converting the motor and drive unit into an explosion-proof structure without impairing the accuracy of measurement, unlike the conventional instruments. It is to be noted that the wind tunnel 51 or 61 is not absolutely required in an actual instrument.

Even with anemometer elements other than hot-wire anemometer elements, advantages equal to or better than those described above can be obtained provided their performance is equal to or better than that of hot-wire anemometer elements, they are inherently explosion-proof and they are small enough to permit their incorporation into the instruments.

Having now fully described the invention, it will be apparent to one of ordinary skill in the art that many changes and modifications can be made thereto without departing from the spirit or scope of the invention as set forth herein.

We claim:

1. A method for estimating the position of leakage and a leakage quantity rate of gas, steam or the like through use of a detection system that includes a plurality of sampling modules arranged in a plant yard to collect samples of a surrounding atmosphere, at least one wind direction and velocity indicator for real-time determination of the direction and velocity of local wind, and at least one sensor module connected to each sampling module for receiving samples of the atmosphere collected by the sampling modules, the sensor modules having a built-in sensor to detect gas, steam or the like in atmosphere received from the sampling module, the method comprising:

estimating an area possibly including a point of leakage of gas, steam or the like with increasing accuracy over the passage of time by analyzing real-time fluctuations in wind direction data and data concerning a position of a sampling module which outputs a corresponding detection signal when the leakage of the gas, steam or the like is discovered;

determining plane coordinates of the center of said area as the plane coordinates of the point of leakage when said area possibly including the point of leakage is narrowed to a relatively small area over the passage of time; and determining the leakage quantity rate by parallel analysis about a certain relational expression which can be established among at least the concentration measured by the sensor module, the wind direction and the wind velocity.

* * * * *